United States Patent [19]

Marcadis et al.

[11] Patent Number: 5,720,726
[45] Date of Patent: Feb. 24, 1998

[54] BALLOON CATHETER HAVING RETENTION ENHANCEMENTS ON THE BALLOON

[75] Inventors: Stuart J. Marcadis, Portage, Ind.; James H. Devries, Grand Rapids, Mich.

[73] Assignee: Medtronic, Inc., Minneapolis, Minn.

[21] Appl. No.: 718,225

[22] Filed: Sep. 20, 1996

Related U.S. Application Data

[63] Continuation of Ser. No. 587,603, Jan. 2, 1996, abandoned, which is a continuation of Ser. No. 250,863, May 27, 1994, Pat. No. 5,487,730, which is a continuation of Ser. No. 999,488, Dec. 30, 1992, abandoned.

[51] Int. Cl.$^6$ ............................................. A61M 29/00
[52] U.S. Cl. ............................................. 604/96; 606/194
[58] Field of Search ........................... 604/104, 107, 604/96, 280; 606/191, 192, 194, 198

[56] References Cited

U.S. PATENT DOCUMENTS

| | | |
|---|---|---|
| 2,927,584 | 3/1960 | Wallace . |
| 3,344,791 | 10/1967 | Foderick . |
| 3,635,223 | 1/1972 | Klieman . |
| 3,815,608 | 6/1974 | Spinosa et al. . |
| 3,970,090 | 7/1976 | Loiacono . |
| 4,465,072 | 8/1984 | Taheri . |
| 4,689,041 | 8/1987 | Corday et al. . |
| 4,721,109 | 1/1988 | Healey . |
| 4,782,834 | 11/1988 | Maguire et al. . |
| 4,927,412 | 5/1990 | Menasche . |
| 5,021,045 | 6/1991 | Buckberg et al. . |
| 5,033,998 | 7/1991 | Corday et al. . |
| 5,041,093 | 8/1991 | Chu . |
| 5,091,205 | 2/1992 | Fan . |
| 5,112,305 | 5/1992 | Barath et al. . |
| 5,158,545 | 10/1992 | Trudell et al. . |
| 5,180,368 | 1/1993 | Garrison . |
| 5,196,024 | 3/1993 | Barath . |
| 5,201,706 | 4/1993 | Noguchi et al. . |
| 5,226,427 | 7/1993 | Buckberg et al. . |
| 5,308,325 | 5/1994 | Quinn et al. . |
| 5,324,260 | 6/1994 | O'Neill et al. . |
| 5,395,331 | 3/1995 | O'Neill et al. . |

FOREIGN PATENT DOCUMENTS

| | | |
|---|---|---|
| 0 204 218 | 12/1986 | European Pat. Off. . |
| 0 249 338 | 5/1987 | European Pat. Off. . |
| 0 416 662 | 3/1991 | European Pat. Off. . |
| 2607706 | 6/1988 | France . |

*Primary Examiner*—Corrine M. McDermott
*Attorney, Agent, or Firm*—Foley & Lardner

[57] ABSTRACT

A catheter for retrograde perfusion of the heart through the coronary sinus, which has an infusion lumen for introducing perfusion liquid into the heart, a retention means such as an inflatable balloon, and can have retention enhancements such as spikes, felt or a hydrophilic coating, on the surface of the retention means to keep it firmly in place.

23 Claims, 6 Drawing Sheets

BALLOON CATHETER HAVING RETENTION ENHANCEMENTS ON THE BALLOON

This is a continuation of application Ser. No. 08/587,603 filed Jan. 2, 1996 now abandoned, which is a continuation of application Ser. No. 08/250,863 filed May 17, 1994 now U.S. Pat. No. 5,487,730 which is a continuation of application Ser. No. 07/999,488 filed Dec. 30, 1992 now abandoned.

BACKGROUND OF THE INVENTION

1. Field of the Invention

This invention relates in general to cardioplegia catheters, and more particularly, to cardioplegia catheters having improved balloons for better retention within a bodily vessel or cavity.

2. Description of Related Art

In performing certain cardiac surgical procedures, it is customary to interrupt the normal function of the heart, an arrested, flaccid heart being much preferred over a beating heart supplied with blood. During such procedures, well-known cardiopulmonary-bypass techniques are employed to isolate the heart from its life-sustaining blood supply.

The process known as cardioplegia, which literally means "heart stop," is used to arrest the beating of the heart, and in some procedures, to provide oxygen to the tissue of the heart. Cardioplegia may be administered in an antegrade manner by introducing the cardioplegic fluid into arteries in the normal direction of blood flow, in a retrograde manner by introducing it into veins in the direction opposite to normal blood flow, or in alternating retrograde and antegrade administration. Cardioplegic solutions, typically containing potassium, magnesium, procaine or a hypocalcemic solution, stop the heart by depolarizing cell membranes.

Retrograde cardioplegia is now conventionally administered by inserting the distal end of a catheter within the heart vessel or cavity known as the coronary sinus, and by forcing the cardioplegic solution through the infusion lumen of the catheter backwards through the coronary veins, in a procedure generally known as retrograde coronary sinus perfusion (RCSP).

Much has been written and continues to be written about this procedure. A comparatively recent example is F. P. Sutter et al., "Continuous retrograde blood cardioplegia", *The Annals of Thoracic Surgery*, Vol. 51, pp. 136–137 (1991).

Catheters for administering RCSP may be equipped with either a manually inflated or self-inflating balloon which surrounds the catheter at its distal end and which, when inflated, engages the wall of the coronary sinus to form a seal. The first type is inflated after the catheter is inserted in the coronary sinus but before flow of cardioplegic solution is initiated. The balloon is typically filled with air from a remote, manually actuated syringe by way of an inflation lumen, provided in a tube carried along the outer surface of the cannula body or formed integrally within the cannula body itself. A self-inflating balloon, on the other hand, is in fluid communication with the infusion lumen of the catheter and is filled with the cardioplegic solution itself when flow is initiated.

During RCSP it is of concern to keep the catheter's balloon firmly situated within the coronary sinus. The wall of the coronary sinus is slippery and expandable, and it tapers in a manner such that the sinus vessel becomes narrower in the direction in which the balloon is advanced during insertion. Placing the balloon well into the coronary sinus ensures good retention. However, several veins open into the coronary sinus very close to its exit into the right atrium, whereby if the balloon is inserted too deeply into the coronary sinus, it may exclude them from perfusion. To ensure adequate perfusion of these veins, the balloon should be positioned just at the opening of the coronary sinus and held there securely to prevent its inadvertent dislodgement during the surgery.

Examples of various expedients intended to assist retention of catheters or similar implements within bodily vessels or cavities have been disclosed in U.S. Pat. Nos. 2,927,584, issued Mar. 8, 1960 to F. J. Wallace; U.S. Pat. No. 3,815,608, issued Jun. 11, 1974 to D. Spinosa et al.; and U.S. Pat. No. 4,721,109, issued Jan. 26, 1988 to M. A. Healey.

An example of such an expedient applied specifically to a balloon catheter for use in RCSP is disclosed in U.S. Pat. No. 4,927,412, issued May 22, 1990 to P. Menasché.

SUMMARY OF THE INVENTION

A catheter according to the invention incorporates a balloon constructed not only to form an effective seal with the wall of the coronary sinus but to retain the balloon securely in a position at or close to the exit of the coronary sinus.

In its broader aspects the invention provides a catheter for supplying perfusion liquid to a bodily vessel having an orifice. The catheter comprises a body having a proximal end, a distal end receivable in the vessel by way of the vessel orifice, and an infusion lumen within the body extending between the proximal end and the distal end and terminating in one or more outlets at the distal end for discharge of liquid from the lumen.

A radially expandable sealing means surrounds the body proximally of the outlet, the sealing means being receivable in the vessel orifice in its unexpanded state and expandable into engagement with the vessel wall to seal the orifice. The sealing means includes retention means adapted to enhance the purchase between the vessel wall and the sealing means in the expanded state to resist removal of the distal end from the vessel and loss of sealing.

In one of the preferred embodiments of the invention, the sealing means comprises, for example, an inflatable balloon, and the retention means comprises a series of protuberances formed on the outer surface of the balloon.

These and other objects, features and advantages of the invention will be apparent from the ensuing description in conjunction with the accompanying drawings.

DESCRIPTION OF THE PREFERRED EMBODIMENTS

Figure 1:
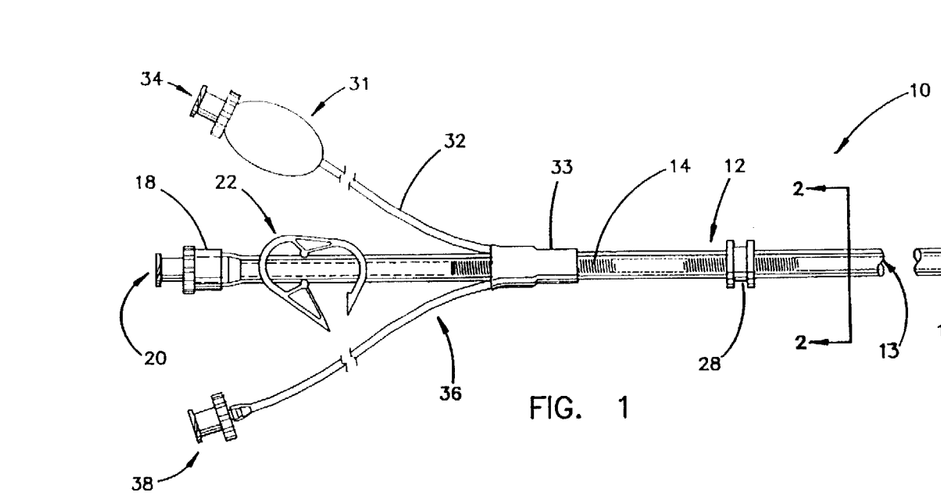
FIG. 1 is a side elevational view of a first embodiment of a catheter according to the invention, incorporating a pleated balloon, shown partially inflated.

Referring now the drawings and to FIG. 1 in particular, a first embodiment of a catheter 10 for the introduction of fluid to a body organ comprises a catheter body 12, a reinforcing spring 14, a sealing/retention balloon 16 and a connector hub 18. The catheter body 12 is preferably formed of a flexible plastic material suitable for introduction into the patient's body. The catheter body 12 is generally tubular in cross section, forming an infusion lumen 13 therethrough.

The coiled reinforcing spring 14 is preferably molded or otherwise embedded into the catheter body 12 to provide strength, support and flexibility for the catheter body 12. For instance, the spring 14 may be assembled into or onto the body 12 and then encapsulated during a coating operation. Typically the spring 14 does not extend entirely to a proximal end 20 of the catheter body 12. A clamping member 22 of conventional design can be mounted on the catheter body 12 adjacent the connector hub 18 and proximal to the spring 14, for squeezing the catheter body 12 to occlude the infusion lumen 13.

The connector hub 18 is mounted on the proximal end 20 of the catheter body. The hub 18 is conventional and is of a suitable configuration for connecting the catheter body 12 to a source of cardioplegic solution. A suture ring 28 is mounted on the catheter body 12 and serves as an aid in securing attachment of the catheter 10 to the heart. The suture ring 28 serves as a structure to which the surgeon can affix a tourniquet 37 (via suture) thus inhibiting movement of the catheter 10 with respect to the heart (see FIG. 3).

The balloon 16 is mounted at a distal end 30 of the catheter body 12. The balloon 16 of the first embodiment is pear-shaped and has retention means, discussed further below, mounted thereon. The balloon 16 of the first embodiment is a manually-inflatable balloon. A balloon inflation lumen 32 extends from the balloon 16 near the distal end 30 of the catheter body 12 to the proximal end 20 of the catheter body 12.

The length of the balloon inflation lumen 32 is preferably integrally molded with the catheter body 12 except for the proximal end of the balloon inflation lumen 32. The proximal end of the inflation lumen exits the catheter body 12 adjacent to proximal end 20 of the catheter body 12. A stress relief-sleeve 33 made of an elastic material surrounds the catheter body 12 and inflation lumen 32 at the point the balloon inflation lumen 32 exits the catheter body 12. An adhesive can be used to help seal the sleeve 33 to the catheter body 12 and the inflation lumen 32.

The balloon 16 is inflated by supplying a pressured fluid or gas to the balloon 16 through the balloon inflation lumen 32. A connector hub 34 is mounted on the proximal end of the balloon inflation lumen 32 for connecting a supply of pressurized fluid or air, such as a syringe. Typically the hub 34 is provided with a releasable check valve for maintaining inflation of the balloon 16.

Figure 2:
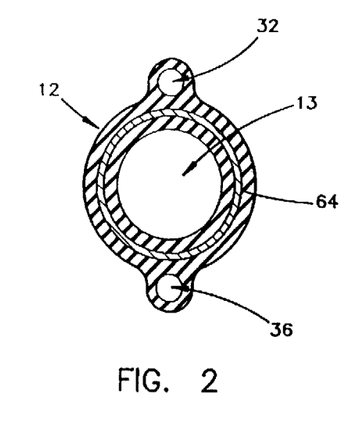
FIG. 2 is a sectional view of a body of the catheter taken along line 2—2 of FIG. 1.

The catheter 10 according to the first embodiment also includes a pressure monitoring lumen 36. Typically the pressure monitoring lumen 36 is integrally molded with the catheter body 12, but can comprise a separate tube either attached or unattached to the length of the catheter body 12. (FIG. 2 shows a cross sectional view of the catheter body 12 showing the infusion lumen 13 and integrally molded inflation and pressure lumens 32 and 36.) The proximal end of the inflation lumen exits the catheter body 12 adjacent to proximal end 20 of the catheter body 12 and is sealed thereto by the sleeve 33.

A connector hub 38 is mounted on the proximal end of the pressure monitoring lumen 36 adjacent the proximal end 20 of the catheter body 12, and is adapted for connection to a pressure monitoring device (not shown). The pressure monitoring lumen 36 terminates at or near the distal end 30 of the catheter body 12 such that the pressure monitoring device is in pressure communication with the inside of the body organ receiving the catheter 10. However, a backup connection may be employed between the pressure monitoring lumen 36 and the infusion lumen 13.

For instance, an opening (not shown) may be provided between the pressure monitoring lumen 36 and the infusion lumen 13 close to the distal end of the catheter 30. If the distal end of the pressure monitoring lumen 36 should become occluded for any reason, accurate pressure readings may still be taken through the opening. Due to the opening's proximity to the distal end of the infusion lumen 13, the magnitude of the pressure measured at its location will be very close to the magnitude of the pressure measured at the distal end of the pressure monitoring lumen 36. For increased accuracy, the pressure measured in such a manner may be corrected for the calculated pressure drop of the perfusion fluid pressure from the location of the opening to the exterior of the infusion lumen 13 at the catheter's distal end 30.

Catheters for retrograde cardioplegia administration employing manually inflatable balloons are well known. For instance, a more detailed description of the aforementioned structure for manually-inflating retrograde balloon catheters can be found in U.S. Pat. No. 4,927,412 issued to Menasché.

Figure 3:
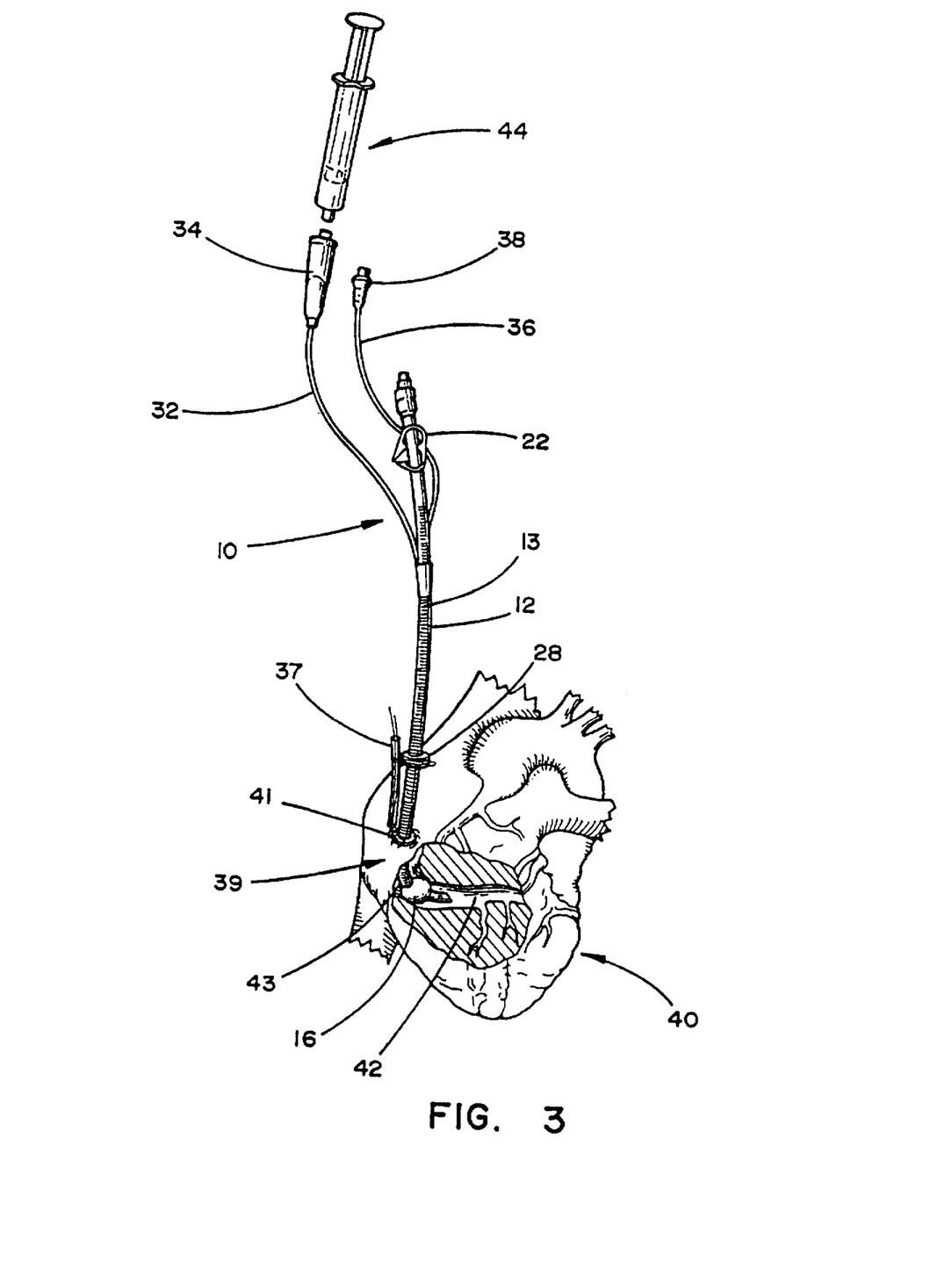
FIG. 3 is a perspective view of the catheter of FIG. 1 positioned in a patient's coronary sinus.
Figure 21:
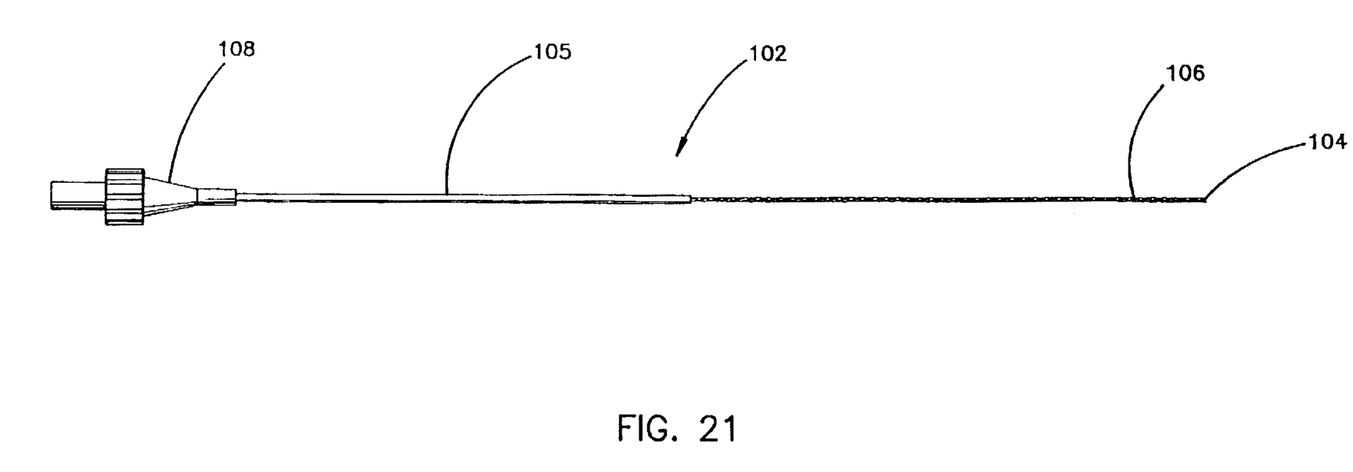
FIG. 21 is a side elevational view of a stylet for use with the catheter according to the invention.

Turning to FIG. 3, the catheter 10 according to the invention, is well suited for supplying cardioplegic solution to the heart muscle 40 during a surgical operation. First, a small incision and purse-string suture 41 is placed in the right atrial wall of the heart 40 and the free ends of the suture 41 are left to extend through a tubular tourniquet 37. A stylet 102 (FIG. 21) is placed inside the catheter 10 to provide rigidity. Typically, the stylet 102 will comprise a rigid proximal section 105 and a malleable distal section 106 extending to a distal tip 104. A handle 108 is provided proximal to the rigid section 105.

The distal end 30 of the catheter body 12, with the stylet 102 in place, is introduced into the right atrium 39 through the purse-string 41 in the heart 40. The catheter body 12 is inserted into the coronary sinus 42 with the balloon 16 in the deflated state until the balloon 16 reaches the sinus ostium 43. The balloon 16 is inflated with a suitable fluid or gas as supplied through the inflation lumen 32 from a syringe 44 or other suitable source. The check valve at the inflation connector hub 34 allows the syringe to be removed while maintaining pressure in the balloon 16. The stylet 102 is then removed, and the occluding clamp 22 is closed. The purse-string 41 is tightened and the tourniquet 37 is clamped with a hemostat (not shown) to keep the purse-string closed. The tourniquet 37 is attached to the suture ring 28 on the catheter body 12 with additional suture material.

Once the balloon 16 of the catheter body 12 is successfully mounted in the sinus ostium 43, thereby sealing the patient's coronary sinus 42, a suitable cardioplegic solution is introduced into the catheter 10 through the connector hub 18. For a retrograde cardioplegia procedure, the solution is under pressure and passes through the infusion lumen and exits the catheter body 12 through an opening 45 in the distal end 30 of the catheter body 12 into the coronary sinus 42 of the patient's heart 40. Additional openings 48 from the perfusion lumen 13 may be provided through the sides of the catheter body 12 near the distal end 20 thereof. The pressurized solution flows into the heart 40 tissue through the veins which normally empty into the coronary sinus 42 and arrests beating of the heart. Depending on the solution used, the solution can also provide necessary oxygen to the heart tissue to prevent damage thereto. The pressure of the cardioplegic solution within the coronary sinus is measured by the pressure sensor (not shown) connected to the pressure lumen 36. Through the use of a pressure sensor, a surgeon can avoid applying excessive pressure to the patient's heart tissue.

The balloon 16 at the distal end of the catheter body 12 of the first embodiment serves two distinct functions in a cardioplegia perfusion process. First, the balloon 16 substantially fills the sinus ostium 43 thereby sealing the coronary sinus 42 from the right atrium 39. The pressurized cardioplegic solution introduced into the coronary sinus 42 through the catheter 10 is forced to flow backwards through the coronary sinus 42 into the veins which typically drain into the coronary sinus 42. Second, the balloon 16 engages the inside circumference of the coronary sinus 42 and sinus ostium 43 and retains the catheter 10 in place during the cardioplegic perfusion process.

During a surgical procedure employing heart perfusion, the surgeon may desire to interrupt the sealing engagement of the balloon 16 with the coronary sinus 42 and allow blood and/or cardioplegia solution to flow out of the coronary sinus 42 into the right atrium 39. In this case, it is desireable to have the balloon 16 quickly assume a low profile in the coronary sinus 42, so as to deflate quickly thereby obstructing the flow as little as possible and quickly relieving fluid pressure within the coronary sinus 42.

Figure 4:
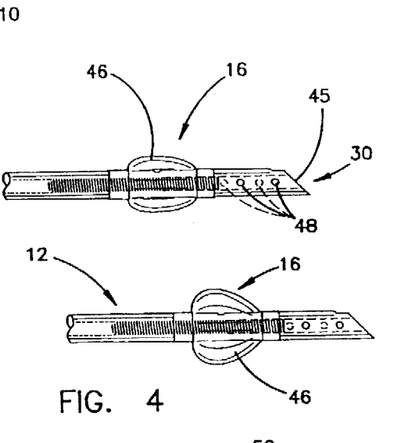
FIG. 4 is a side elevational view of the fully inflated balloon of the catheter of FIG. 1.
Figure 5:
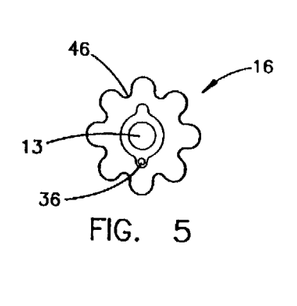
FIG. 5 is an end elevational view of the partially inflated balloon of the catheter of FIG. 1.

The balloon 16 employed on the first embodiment of the catheter 10 according to the invention is particularly well suited to quickly deflate. As shown in FIGS. 1, 4 and 5, the balloon 16 of the first embodiment is provided with a plurality of longitudinal striations 46. When the balloon 16 is not fully inflated as seen in FIGS. 1 and 5, the striations 46 cause the balloon to fold into an accordion fold. The deflated accordion folding of the balloon 16 provided by the striations 46 improves flow of blood past the balloon and quickly relieves pressure within the coronary sinus 42. As shown in FIG. 4, when the balloon 16 is fully inflated, the striations 46 have no effect on the balloon's 16 shape thereby permitting effective engagement of the balloon with the interior surface of the coronary sinus 42, providing an effective seal to prevent fluid flow.

Figure 6:
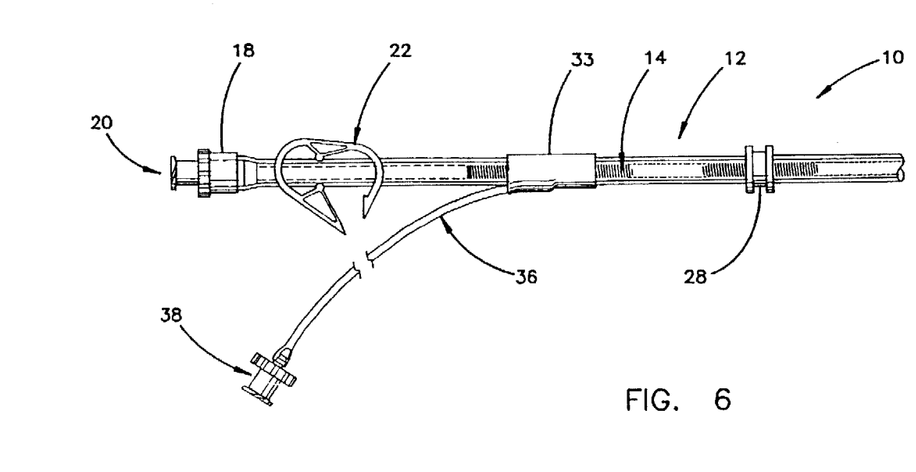
FIG. 6 is a side elevational view of a second embodiment of a catheter according to the invention, provided with a self-inflating balloon incorporating small protuberances on the balloon for improved retention.

As seen in FIG. 6, a second embodiment of the balloon catheter 10 according to the invention incorporates a self-inflating balloon 50 near the distal end 30 of the catheter body 12. In this embodiment, the catheter 10 does not incorporate a lumen for inflating the balloon, rather the balloon 50 is inflated by the cardioplegic solution flowing through the catheter body 12. The infusion lumen 13 of the catheter body 12 is in fluid communication with the balloon 50 through at least one balloon inflation aperture 52. As pressurized fluid is forced from the connector hub 18 through the infusion lumen, it enters and inflates the self-inflating balloon 50. The fluid also flows out the distal end 30 of the catheter body 12. When the source of pressurized solution applied to the connector hub 18 is removed, the self-inflating balloon 50 will deflate.

Several methods are known for forming a self inflating balloon 50 according to the invention. A flow restriction of some form is needed to supply the necessary back pressure on the balloon 50 to cause it to inflate in response to the fluid pressure of the perfusion fluid. For instance, the infusion lumen exits 45, 48 can be restricted in size, thus causing a pressure drop across the restriction. However, large lumen exits 45, 48 have several advantages unrelated to balloon pressure. For instance, larger exits are less likely to be occluded by contact with the coronary sinus 42 or particles therein. Also, a larger exit provides a gentler flow pattern of perfusion fluid out of the infusion lumen 13 which is less likely to stress the coronary sinus. Thus, the distal end 30 of the catheter 10 is angled relative to the catheter body 12 to enlarge the infusion lumen exit 45. The angled distal end 30 of the catheter 10 also aids in introducing the catheter 10 into the coronary sinus ostium 43. The total exit area is increased by the additional exits 48 in the sides of the catheter body 12.

The balloon 50 shown in FIG. 6 restricts flow internal to the catheter 10 to provide the backpressure for filling the balloon 50. A plug 54 in the infusion lumen 13 forces all of the perfusion fluid flowing through the infusion lumen 13 to enter the balloon 50 through the balloon inflation apertures 52. At least one balloon exit aperture 56 is provided distal to the plug 54 and allows the flow to leave the balloon 50 and reenter the infusion lumen 13. The aggregate cross sectional area of the exit apertures 56 is less than the aggregate cross sectional area of the balloon inflation apertures 52 providing a positive pressure internal to the balloon 50 to keep the balloon 50 inflated during flow of the perfusion fluid.

The internal surface of the coronary sinus 42 receiving the catheter 10 is slippery, somewhat extensible and expands in the direction of its ostium 43 into the right atrium 39. Several of the smaller veins which normally drain deoxygenated blood from the heart 40 enter the coronary sinus 42 near its ostium 43. To keep the catheter 10 firmly ensconced in the coronary sinus 42, the balloon 50 should be placed far inside the coronary sinus 42. On the other hand, to make sure that all areas of the heart 40 are properly perfused, the balloon should be placed as close to the sinus ostium 43 as possible.

By increasing the friction between the balloon 50 and the coronary sinus 42, the balloon 50 can be placed closer to the ostium yet still provide adequate retention. Several methods for retention of the catheter 10 inside of the coronary sinus 42 will be described with reference to the self inflating balloon 50. However, the methods for improved retention disclosed herein are equally applicable to the manually inflating balloon 16.

The balloon 50 is provided with various gripping enhancements to provide improved engagement of the balloon 50 with the wall of the coronary sinus 42. In FIG. 6, the balloon 50 is shown with a mammillated outer surface having a plurality of small spikes 58 formed thereon. The spikes 58 are preferably formed into the polymer material of the balloon during molding. The spikes 58 aid the balloon 50 in gripping the walls of the coronary sinus 42, whereas the flat surface of the balloon 50 seals the coronary sinus 42.

Figure 7:
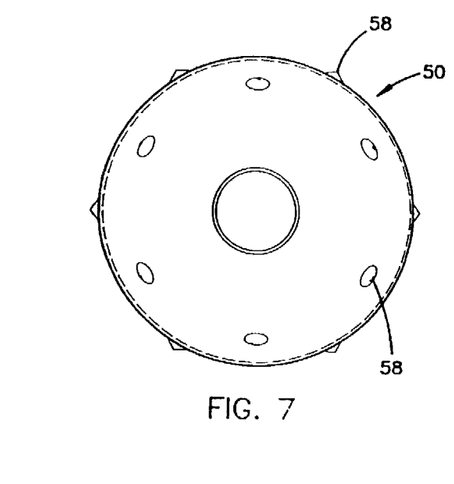
FIG. 7 is an end elevational view of the balloon of the catheter of FIG. 6, as viewed from the proximal end of the balloon.
Figure 8:
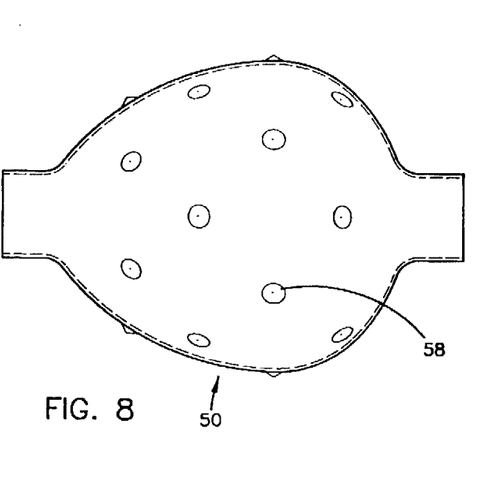
FIG. 8 is a side elevational view of the balloon of the catheter of FIG. 6.
Figure 9:
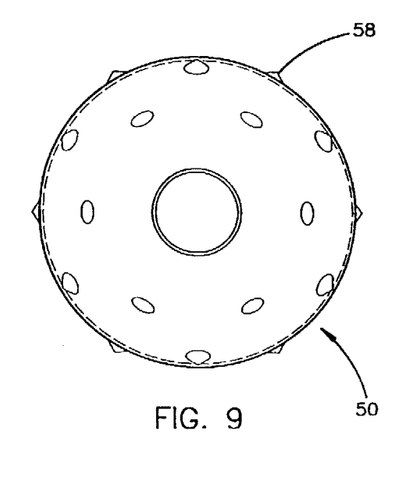
FIG. 9 is an end elevational view of the balloon of the catheter of FIG. 6, as viewed from the distal end of the balloon.

FIGS. 7 to 9 show the balloon 50, removed from the catheter body 12 for clarity, and show the detail of arrangement of the plurality of spikes 58 of the balloon 50 of the second embodiment. The spikes 58 are arranged around the entire circumference of the balloon 50 in a spaced relationship. The spikes 58 are low, broad, solid cones, attached at the base to the outer surface of the balloon 50. The pointed tips of the conical spikes 58 improve the gripping ability of the balloon 50. The spikes 58 may also have a hollow interior open to the interior of the balloon 50. The sealing/retention balloon 50 of the second embodiment is preferably pear-shaped for improved seal, and decreased occlusion of the veins adjacent the sinus ostium 43.

Figure 10:
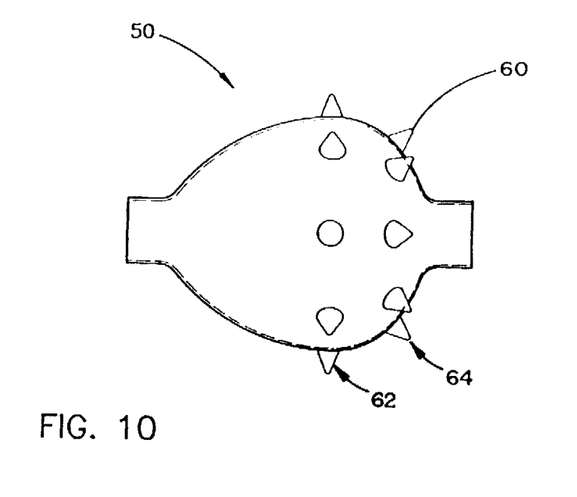
FIG. 10 is a side elevational view of a balloon of a third embodiment of a catheter according to the invention, incorporating protuberances in the form of a relatively large number of large spikes on the proximal end of the balloon for improved retention.
Figure 11:
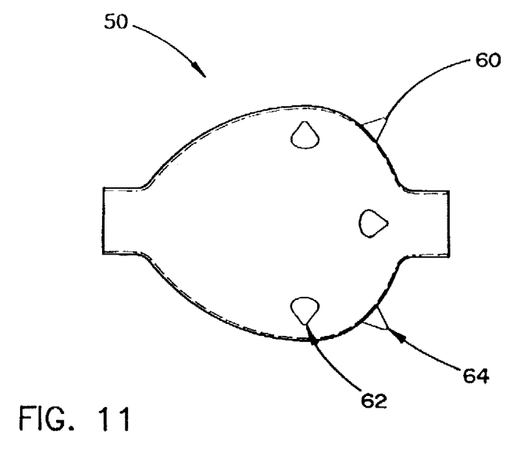
FIG. 11 is a side elevational view of a balloon of a fourth embodiment of the catheter according to the invention, incorporating protuberances in the form of a relatively small number of large spikes on the proximal end of the balloon for improved retention.

Third and fourth embodiments of the catheter, shown respectively in FIGS. 10 and 11, employ relatively larger, longer spikes 60 on the balloon 50. The spikes 60 are preferably located only on the wider proximal portion of the balloon 50 in contact with the wall of the coronary sinus 42. FIG. 10 shows the spikes 56 arranged in two annular rows; a first row 62 about the widest portion of the balloon 50 wherein the spikes extend generally radially outwardly from and normal to the catheter body 12 (not shown in FIG. 10) and a second row 64, proximal to the first row 62, wherein the spikes 60 extend outwardly radially from the balloon 50 and at an angle to the catheter body 12. The angle of the spikes 60 in the second row 64 is such that the spikes 60 project proximally to provide better purchase in a direction to prevent the balloon 50 from moving outwardly of the coronary sinus 42. The balloon 50 shown in FIG. 11 has the spikes 60 arranged in two rows 62, 64 similarly to FIG. 10, but employs fewer spikes 60.

Figure 12:
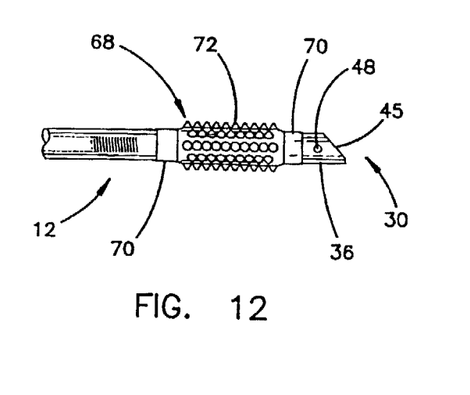
FIG. 12 is a side elevational view of an elastic balloon of a fifth embodiment of a catheter according to the invention, incorporating protuberances in the form of a large number of small spikes extending over the length of the balloon for improved retention, the balloon being in the deflated condition.
Figure 13:
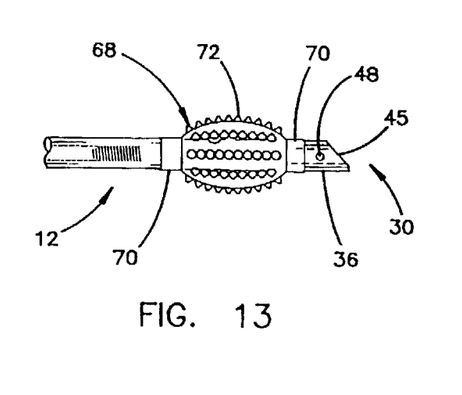
FIG. 13 is a side elevational view of the balloon of FIG. 12 in the inflated condition.

A fifth embodiment of the catheter 10 is shown in FIGS. 12 and 13, and employs a manually inflatable elastic balloon 68. Whereas the balloons 16 and 50 of the previous embodiments are preferably formed of relatively inelastic polymers, the elastic balloon 68 of FIGS. 12 and 13 is formed of an elastomeric polymer. The balloon 68 is formed of a tubular elastomeric material, which is placed over the catheter body 12. Each end of the balloon 68 is affixed to the catheter body 12, and a sealing band 70 is preferably provided to improve the seal thereof. As in the first embodiment, the inflation lumen 32 is in communication with the balloon 68 such that the balloon 68 can be inflated with a suitable fluid or gas.

The balloon 68 shown in FIGS. 12 and 13 is provided with a plurality of spikes 72 for improved gripping of the coronary sinus 42. The spikes are preferably mounted closely adjacent to one another in longitudinal rows parallel to the longitudinal axis of the catheter body 12. FIG. 12 depicts the balloon 68 in the deflated state, whereas FIG. 13 shows the balloon 68 fully inflated.

Figure 14:
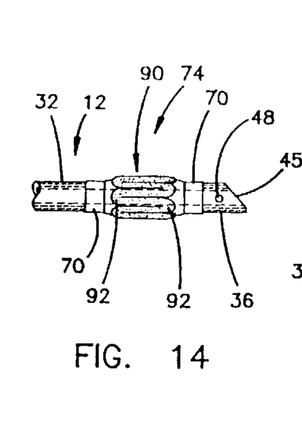
FIG. 14 is a side elevational view of a balloon of a sixth embodiment of a catheter according to the invention, incorporating a continuous felt strip for improved retention, the balloon being in the deflated condition.
Figure 15:
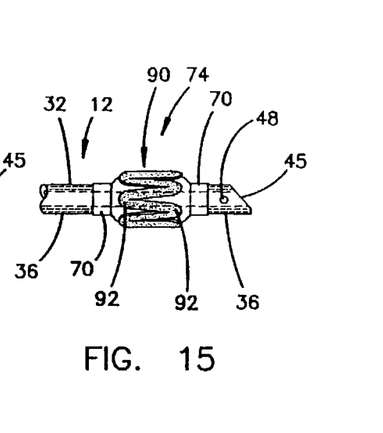
FIG. 15 is a side elevational view of the balloon of FIG. 14 in the inflated condition.

A sixth embodiment of the catheter 10 employing an improved retention means for a balloon 74 is shown in FIGS. 14 and 15. In this embodiment, the retention means comprises a continuous strip of felt 90. Preferably, the felt strip 90 is mounted on the outside surface of the balloon 74 in a zigzag pattern, such that the balloon 74 may expand while keeping the felt strip 90 continuous.

When the balloon is in the contracted state, as shown in FIG. 14, the individual loops 92 of the zigzag pattern abut each other about the circumference of the balloon 74. When the balloon is inflated, as seen in FIG. 15, the loops 92 permit the felt strip 90 to expand until the strip 90 contacts the interior surface of the coronary sinus 42. In light of the zigzag pattern of the felt strip 90, there is a relatively large area of surface contact between the retention means and the interior surface of the coronary sinus 42.

Figure 16:
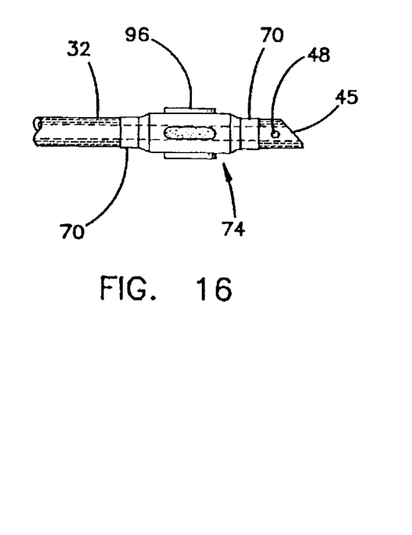
FIG. 16 is a side elevational view of a balloon of a seventh embodiment of a catheter according to the invention, incorporating felt patches for improved retention, the balloon being in the deflated condition.

A seventh embodiment of the catheter 10 according to the invention is shown in FIG. 16, wherein the retention-means comprise a plurality of oval felt patches 96 arranged about the circumference of the balloon 74. As in the sixth embodiment, the felt patches 96 do not contact the interior surface of the coronary sinus 42 in the retracted state. Rather, when the balloon 74 is inflated, the felt patches 96 engage the interior surface and frictionally hold the catheter 10 in place with respect to the coronary sinus 42. Although oval-shaped patches 96 are disclosed in FIG. 16, it is understood that other shapes and arrangements of felt members can be used. Preferably, the patches are formed of a thin Dacron pledget material.

The balloon 74 shown in FIGS. 14 to 16 is tubular, affixed by means of sealing bands 70 as in the fifth embodiment, and may be constructed of either elastic or inelastic polymer material. The balloon 74 is adapted for manual inflation by means of the inflation lumen 32. However, the zigzag continuous felt strip 90 of the sixth embodiment and the felt pads 96 of the seventh embodiment are suitable for use on other balloons such as the pear shaped manually inflatable and self inflatable balloons 16 and 50 and the elastic balloon 68.

Figures 17, 18:
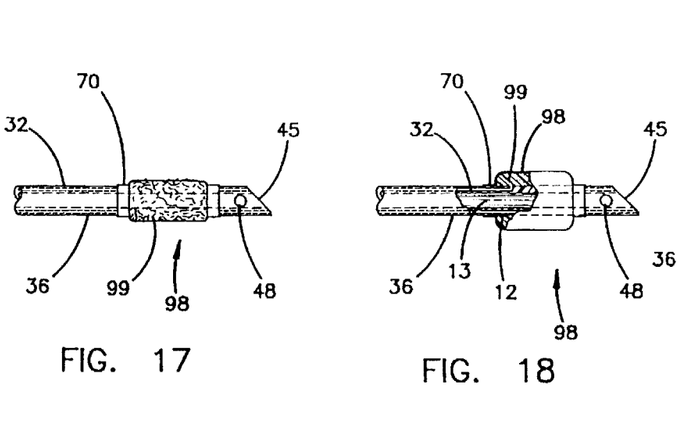
FIG. 17 is a side elevational view of a balloon of an eighth embodiment of a catheter according to the invention and incorporating a foam insert, the balloon being in the deflated condition.
FIG. 18 is a side elevational view of the balloon of FIG. 17 in the inflated condition.

An eighth embodiment of the retention means according to the invention is disclosed in FIGS. 17 and 18. In this embodiment, a balloon 98 is filled with a low density foam 99. In its equilibrium state, the foam-filled balloon 98 is fully inflated, as seen in FIG. 18. When a vacuum or negative pressure is applied to the foam-filled balloon 98 through the inflation lumen 32, the balloon contracts to a deflated state as seen in FIG. 17.

In use, the surgeon would apply a vacuum or lower pressure to the foam-filled balloon 98 through the inflation lumen 32 with a syringe 44 causing the balloon to contract to its deflated state. When the catheter 10 is mounted in the desired position within the coronary sinus 42, the negative pressure on the foam-filled balloon 98 is released, thereby permitting the foam to expand to its equilibrium state such that it engages the interior surface of the coronary sinus 42 and prevents movement of the catheter 10 with respect to the coronary sinus 42. The foam-filled balloon 98 may be provided with any of the previous surface enhancements, either alone or in combinations. For instance, surface spikes 58 and felt pads 56 may be applied to the balloon's 98 outer surface.

Figure 19:
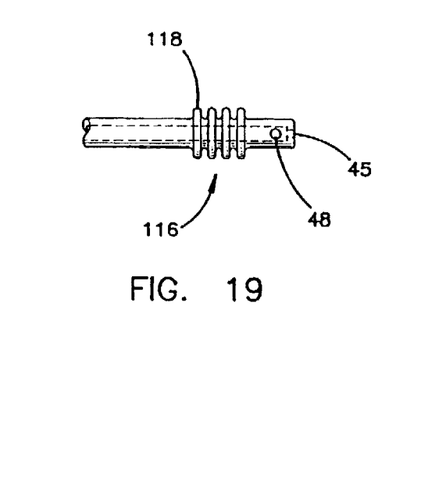
FIG. 19 is a side elevational view of a retention means of a ninth embodiment of a catheter according to the invention and incorporating an accordion pleated tip, the tip being in the radially expanded condition.
Figure 20:
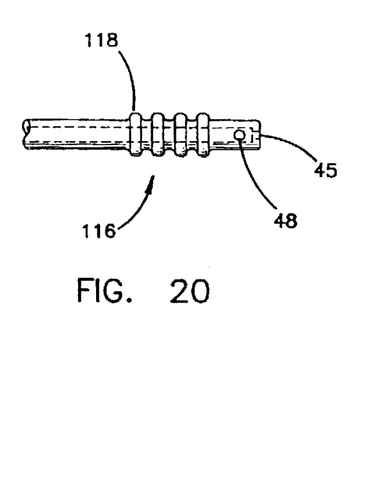
FIG. 20 is a side elevation view of the retention means of FIG. 19, the tip being in the radially unexpanded or retracted condition.

A ninth embodiment of the catheter 10 according to the invention comprises an expandable accordion tip 116, as seen in FIGS. 19 and 20. The accordion tip 116 comprises several pleats 118 formed from elastic material extending radially outwardly from the catheter body 12. The infusion lumen exit 45 at the distal end of the tip 116 is restricted or otherwise formed to capture the tip 104 of the stylet 102.

The pleats are radially retracted, as seen in FIG. 20, by inserting the stylet 102 into the catheter body 12 lumen 13 until the malleable wire 106 contacts the tip 116 distal to the accordion pleats 118. A sufficient force is applied to the stylet 102 with respect to the catheter body 12 to overcome the resilient force of the pleats 118, thereby expanding the pleats 118 longitudinally and retracting the pleats 118 radially. In the pleat's 118 radially retracted state, the catheter 10 is inserted into the coronary sinus 42. The stylet 102 is then removed permitting the pleats 118 to expand to their equilibrium condition.

Figure 22:
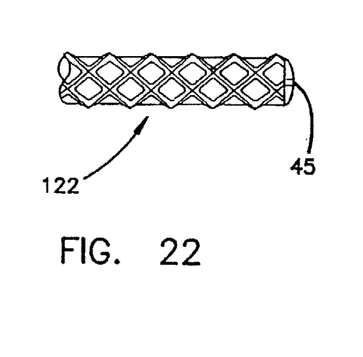
FIG. 22 is a side elevational view of a retention means of a tenth embodiment of a catheter according to the invention and incorporating a lattice structure, the lattice structure being in the radially expanded condition.
Figures 23, 24:
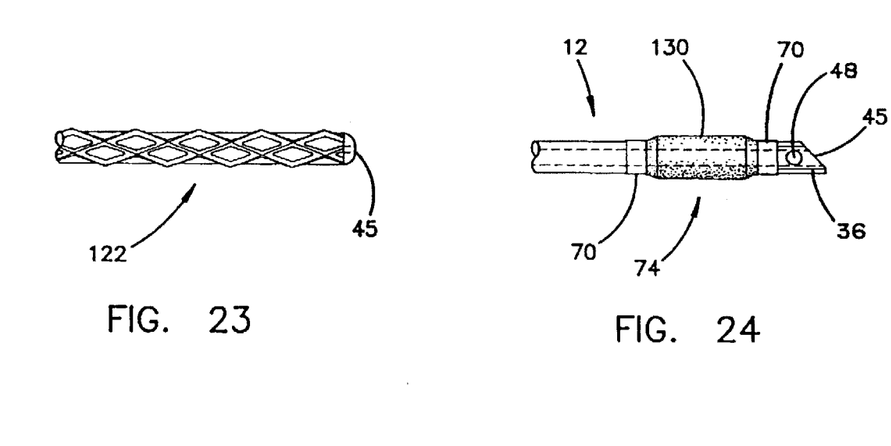
FIG. 23 is a side elevational view of the retention means of FIG. 22 in the radially unexpanded or retracted condition.
FIG. 24 is a side elevational view of a balloon of an eleventh embodiment of a catheter according to the invention and incorporating a hydrophilic coating for improved retention, the balloon being in the deflated condition.

FIGS. 22 and 23 show a tenth embodiment of the catheter 10 according to the invention wherein the distal end of the catheter body 12 is provided with an interwoven lattice structure 122, similar to the common Chinese finger tube. The infusion lumen exit 45 is restricted or otherwise formed to capture the tip 104 of the stylet 102, as in the previous embodiment. In its equilibrium state, as seen in FIG. 22, the lattice structure 122 is radially expanded and of a diameter sufficient to contact the interior surface of the coronary sinus 42. The diameter of the lattice structure 122 is reduced by inserting the stylet 102 in the catheter body 12 until it contacts the distal tip of the catheter 30 and extends the interwoven lattice structure 122, thereby decreasing the diameter of the lattice structure 122, as seen in FIG. 23.

An eleventh embodiment of the catheter 10 according to the invention, as seen in FIG. 24, wherein the balloon 74 incorporates a hydrophilic coating 130 on its outer surface. The hydrophilic coating 130 is highly absorbent and adheres to the interior surface of the coronary sinus 42 once the balloon 74 is inflated and placed into contact with the coronary sinus 42. Although shown on the tubular balloon 74, the hydrophilic coating 130 is applicable to any balloon design for use on a catheter.

While particular embodiments of the invention have been shown, it will be understood, of course, that the invention is not limited thereto since modifications can be made by those skilled in the art, particularly in light of the foregoing teachings. Reasonable variation and modification are possible within the foregoing disclosure of the invention without departing from its true spirit an scope. For instance, each of the embodiments showed the retention means spaced a slight distance proximal to the distal end 30 of the catheter 10. However, the retention means, especially the self inflating balloons, can be placed at the distal end 30 of the catheter 10 with the infusion lumen exit 45 located either in or at the distal end of the retention means. Any of the methods for improved retention are also appropriate for plug style retention means, such as a nondeflatable foam filled balloon, or even rigid plugs.

While the invention has been particularly described in connection with certain specific embodiments thereof, it is to be understood that this is by way of illustration and not of limitation, and the scope of the appended claims should be construed as broadly as the prior art will permit.

What is claimed is:

1. An elongated flexible catheter for supplying perfusion liquid to a bodily vessel having an orifice, the catheter comprising:

a catheter body having a longitudinal axis, a proximal end, a distal end receivable in a vessel by way of the vessel orifice, and an infusion lumen formed within the body and extending between the proximal and distal ends;

at least one infusion lumen outlet provided at the distal end of the catheter body for discharge of liquid from the lumen; and a radially expandable sealing member mounted to and surrounding the catheter body proximally of the at least one infusion lumen outlet the sealing member having an outer surface and being expandable between a retraced state and an expanded state, in the retracted state the sealing member is receivable in the orifice and in the expanded state, the sealing member is adapted to contact the vessel wall and substantially seal the orifice;

the sealing member including a plurality of protuberances provided on the outer surface thereof extending outwardly therefrom, each protuberance comprising:

a base having a center point provided on the outer surface of the sealing member;

a tip provided a spaced distance from the base; and a protuberance axis extending between the tip and the center point of the base, the protuberance axis of each of at least a portion of said plurality of protuberances being substantially normal to the outer surface of the sealing member wherein the protuberances are adapted to enhance the purchase between the vessel wall and the sealing member in the expanded state, and the protuberances are spaced about the sealing member to resist both proximal and distal movement of the sealing member with respect to the vessel wall.

2. A catheter according to claim 1 wherein the tip of each of the protuberances is pointed.

3. A catheter according to claim 1 wherein the protuberances are arranged in at least one row parallel to the longitudinal axis of the catheter body.

4. A catheter according to claim 1 wherein the protuberances are of a conical form.

5. A catheter according to claim 1 wherein each of the protuberances has a height defined by the distance between the tip and the center point of the base and the height of each of the protuberances is less than the diameter of the base thereof.

6. A catheter according to claim 1 wherein each of the protuberances has a height defined by the distance between the tip and the center point of the base and the height of each of the protuberances is greater than or equal to the diameter of the base thereof.

7. A catheter according to claim 1 wherein the protuberances are arranged in at least one circumferential row about a diameter of the sealing member.

8. A catheter according to claim 1 wherein the protuberances are arranged in at least two circumferential rows about respective diameters of the sealing member, and in the expanded state of the sealing member, a first row is oriented so that its protuberances extend radially outwardly with respect to the catheter body, and a second row is oriented so that its protuberances extend outwardly and proximally with respect to the catheter body.

9. An elongated flexible catheter for supplying perfusion liquid to a bodily vessel having an orifice, the catheter comprising:

a catheter body having a longitudinal axis, a proximal end, a distal end receivable in a vessel by way of the vessel orifice, and an infusion lumen formed within the body and extending between the proximal and distal ends;

at least one infusion lumen outlet provided at the distal end of the catheter body for discharge of liquid from the lumen; and a radially expandable sealing member mounted to and surrounding the catheter body proximally of the at least one infusion lumen outlet, the sealing member having an outer surface and being expandable between a retracted state and an expanded state, in the retracted state the sealing member is receivable in the orifice and in the expanded state, the sealing member is adapted to contact the vessel wall and substantially seal the orifice;

the sealing member including a plurality of protuberances provided on the outer surface thereof extending outwardly therefrom adapted to enhance the purchase between the vessel wall and the sealing member in the expanded state thereby resisting movement of the catheter body with respect to the vessel and loss of the seal, wherein the protuberances are arranged in at least one row parallel to the longitudinal axis of the catheter body.

10. A catheter according to claim 9 wherein each protuberance comprises:

a base having a center point provided on the outer surface of the sealing member;

a tip provided a spaced distance from the base; and a protuberance axis extending between the tip and the center point of the base, the protuberance axis of each of at least a portion of said plurality of protuberances being substantially normal to the outer surface of the sealing member.

11. A catheter according to claim 9 wherein the protuberances are of a conical form.

12. An elongated flexible catheter for supplying perfusion liquid to a bodily vessel having an orifice, the catheter comprising:

a catheter body having a longitudinal axis, a proximal end, a distal end receivable in a vessel by way of the vessel orifice, and an infusion lumen formed within the body and extending between the proximal and distal ends;

at least one infusion lumen outlet provided at the distal end of the catheter body for discharge of liquid from the lumen; and a radially expandable sealing member mounted to and surrounding the catheter body proximally of the at least one infusion lumen outlet, the sealing member having an outer surface and being expandable between a retracted state and an expanded state, in the retracted state the sealing member is receivable in the orifice and in the expanded state, the sealing member is adapted to contact the vessel wall and substantially seal the orifice;

the sealing member including a plurality of protuberances provided on the outer surface thereof extending outwardly therefrom adapted to enhance the purchase between the vessel wall and the sealing member in the expanded state thereby resisting movement of the catheter body with respect to the vessel and loss of the seal, wherein the protuberances are arranged in at least two circumferential rows about respective diameters of the sealing member, and in the expanded state of the sealing member, a first row is oriented so that its protuberances extend radially outwardly with respect to the catheter body, and a second row is oriented so that its protuberances extend outwardly and distally with respect to the catheter body.

13. A catheter according to claim 12 wherein each protuberance comprises:

a base having a center point provided on the outer surface of the sealing member;

a tip provided a spaced distance from the base; and a protuberance axis extending between the tip and the center point of the base, the protuberance axis of each of at least a portion of said plurality of protuberances being substantially normal to the outer surface of the sealing member.

14. An elongated flexible catheter for supplying perfusion liquid to a bodily vessel having an orifice, the catheter comprising:

a catheter body having a longitudinal axis, a proximal end, a distal end receivable in a vessel by way of the vessel orifice, and an infusion lumen formed within the body and extending between the proximal and distal ends;

at least one infusion lumen outlet provided at the distal end of the catheter body for discharge of liquid from the lumen; and a radially expandable sealing member mounted to and surrounding the catheter body proximally of the at least one infusion lumen outlet, the sealing member having an outer surface and being expandable between a retracted state and an expanded state, in the retracted state the sealing member is receivable in the orifice and in the expanded state, the sealing member is adapted to contact the vessel wall and substantially seal the orifice;

the sealing member including a plurality of protuberances provided on the outer surface thereof adapted to enhance the purchase between the vessel wall and the sealing member in the expanded state to resist movement of the catheter body with respect to the vessel and loss of the seal, each protuberance comprising:

a base provided on the outer surface of the sealing member, the base having a center point;

a tip provided a spaced distance from the base; and a protuberance axis extending between the tip and the center point of the base, and in the expanded state the protuberance axis of each of at least a portion of said plurality of protuberances extending radially outwardly and distally with respect to the catheter body and the protuberance axis of at least another portion of said plurality of protuberances extending, with respect to the catheter body, radially outwardly and proximally.

15. A catheter according to claim 14 wherein the protuberances are arranged in at least one row parallel to the longitudinal axis of the catheter body.

16. A catheter according to claim 14 wherein the tip of each of the protuberances is pointed.

17. A catheter according to claim 14 wherein the protuberances are arranged in at least three circumferential rows about respective diameters of the sealing member, and a first row is oriented so its protuberances extend proximally wherein a third one of the rows is oriented so that its protuberances extend outwardly and distally with respect to the catheter body.

18. A catheter according to claim 14 wherein the protuberances are of a conical form and extend generally radially outwardly from the outer surface of the sealing member.

19. A catheter according to claim 14 wherein each of the protuberances has a height defined by the distance between the tip and the base and the height of each of the protuberances is less than the diameter of the base thereof.

20. A catheter according to claim 14 wherein each of the protuberances has a height defined by the distance between the tip and the base and the height of each of the protuberances is greater than or equal to the diameter of the base thereof.

21. A catheter according to claim 14 wherein the protuberances are arranged in at least one circumferential row about a diameter of the sealing member.

22. A catheter according to claim 14 wherein the protuberances are arranged in at least two circumferential rows about respective diameters of the sealing member, and in the expanded state of the sealing member, a first row is oriented so that its protuberances extend radially outwardly with respect to the catheter body, and a second row is oriented so that its protuberances extend outwardly and proximally with respect to the catheter body.

23. A catheter according to claim 22 and further comprising a third circumferential row of protuberances arranged about a diameter of the sealing member, the third row is oriented so that its protuberances extend outwardly and distally with respect to the catheter body when the sealing member is in the expanded state.

* * * * *